United States Patent [19]
Zimmerman et al.

[11] Patent Number: 4,988,981
[45] Date of Patent: Jan. 29, 1991

[54] COMPUTER DATA ENTRY AND MANIPULATION APPARATUS AND METHOD

[75] Inventors: Thomas G. Zimmerman, San Francisco; Jaron Z. Lanier, Palo Alto, both of Calif.

[73] Assignee: VPL Research, Inc., Redwood City, Calif.

[21] Appl. No.: 317,107

[22] Filed: Feb. 28, 1989

Related U.S. Application Data

[63] Continuation of Ser. No. 26,930, Mar. 17, 1987, abandoned.

[51] Int. Cl.⁵ .............................................. G09G 3/02
[52] U.S. Cl. .................................................... 340/709
[58] Field of Search .............. 340/709, 706, 712, 705, 340/725, 6; 352/50

[56] References Cited

U.S. PATENT DOCUMENTS

| | | |
|---|---|---|
| 1,335,272 | 3/1920 | Broughton . |
| 2,356,267 | 8/1944 | Pelunis . |
| 3,510,210 | 5/1970 | Haney ................................... 352/50 |
| 3,777,086 | 12/1973 | Riedo . |
| 4,059,830 | 11/1977 | Threadgill . |
| 4,074,444 | 2/1978 | Laenger et al. ................. 340/365 R |
| 4,209,255 | 6/1980 | Heynau et al. ........................ 340/707 |
| 4,302,138 | 11/1981 | Zarudiansky . |
| 4,355,805 | 10/1982 | Baer et al. ............................ 340/709 |
| 4,408,495 | 10/1983 | Couch et al. . |
| 4,414,537 | 11/1983 | Grimes ............................ 340/365 S |
| 4,414,984 | 11/1983 | Zarudiansky . |
| 4,524,348 | 6/1985 | Lefkowitz ........................ 340/365 R |
| 4,540,176 | 9/1985 | Baer . |
| 4,542,291 | 9/1985 | Zimmerman . |
| 4,544,988 | 10/1985 | Hochstein . |
| 4,553,393 | 11/1985 | Ruoff . |
| 4,558,704 | 12/1985 | Petrofsky . |
| 4,565,999 | 1/1986 | King et al. ........................ 340/707 |
| 4,569,599 | 2/1986 | Bölkow et al. ......................... 356/5 |
| 4,579,006 | 4/1986 | Hosoda . |
| 4,581,491 | 4/1986 | Boothroyd . |
| 4,586,335 | 5/1986 | Hosoda et al. . |
| 4,586,387 | 5/1986 | Morgan et al. . |
| 4,613,139 | 9/1986 | Robinson, II . |
| 4,634,856 | 1/1987 | Kirkham . |
| 4,654,520 | 3/1987 | Griffiths . |
| 4,654,648 | 3/1987 | Herrington et al. ................. 340/706 |
| 4,660,033 | 4/1987 | Brandt . |
| 4,665,388 | 5/1987 | Ivie et al. . |
| 4,682,159 | 7/1987 | Davison ............................. 340/709 |
| 4,711,543 | 12/1987 | Blair et al. ............................. 352/50 |
| 4,715,235 | 12/1987 | Fukui et al. . |

FOREIGN PATENT DOCUMENTS

| | | |
|---|---|---|
| 3442549 | 11/1984 | Fed. Rep. of Germany . |
| 3334395 | 4/1985 | Fed. Rep. of Germany . |
| 1225525 | 4/1986 | U.S.S.R. . |

OTHER PUBLICATIONS

Fisher et al., "Virtual Environment Display System", ACM 1986 Workshop on Interactive 3D Graphics, Oct. 23-24, 1986, Chapel Hill, N.C.

(List continued on next page.)

*Primary Examiner*—Alvin E. Oberley
*Attorney, Agent, or Firm*—Townsend and Townsend

[57] ABSTRACT

Apparatus is disclosed for generating control signals for the manipulation of virtual objects in a computer system according to the gestures and positions of an operator's hand or other body part. The apparatus includes a glove worn on the hand which includes sensors for detecting the gestures of the hand, as well as hand position sensing means coupled to the glove and to the computer system for detecting the position of the hand with respect to the system. The computer system includes circuitry connected to receive the gesture signals and the hand position signals for generating control signals in response thereto. Typically, the control signals are used to manipulate a graphical representation of the operator's hand which is displayed on a monitor coupled to the computer system, and the graphical representations of the operator's hand manipulates virtual objects or tools also displayed by the computer.

66 Claims, 5 Drawing Sheets

OTHER PUBLICATIONS

The Human Interface in Three Dimensional Computer Art Space by Jennifer A. Hall, B.F.A., Kansas City Art Institute 1980.

Human Body Motion As Input to an Animated Graphical Display by Carol Marsha Ginsberg, B.S., Massachusetts Institute of Technology, 1981.

Put-That-There: Voice and Gesture at the Graphics Interface by Richard A. Bolt, Massachusetts Institute of Technology, 1980.

Proceedings, SPIE Conference on Processing and Display of Three-Dimensional Data-Interactive Three-Dimensional Computer Space-by Christopher Schmandt, Massachusetts Institute of Technology, 1982.

"One-Point Touch Input of Vector Information for Computer Displays", C. Herot and G. Weinzapfel, *Computer Graphics*, vol. 12, No. 3, Aug. 1978.

"Digital Actuator Utilizing Shape Memory Effect", Honma, et al. lecture given at 30th Anniversary of TOKAI Branch foundation on Jul. 14, 1981.

"Micro Manipulators Applied Shape Memory Effect", Honma et al., paper presented at 1982 Precision Machinery Assoc. Autumn Conference of Oct. 20. (Also in Japanese).

"Magnetoelastic Force Feedback Sensors for Robots and Machine Tools", John M. Vranish, *National Bureau of Standards,* Code 738.03.

"Analysis of Muscle Open and Closed Loop Recruitment Forces: Preview to Synthetic Proprioception", Solomonow, et al., *IEE Frontier of Engineering and Computing in Health Care,* 1984.

"Shape Memory Effect Alloys for Robotic Devices", Schetky, L. *Robotics Age,* Jul. 1984, pp. 13-17.

"Laboratory Profile", R & D Frontiers.

"Hitachi's Robot Hand", *Robotics Age,* Jul. 1984.

COMPUTER DATA ENTRY AND MANIPULATION APPARATUS AND METHOD

This a continuation of application Ser. No. 07/026,930, filed Mar. 17, 1987, now abandoned.

BACKGROUND OF THE INVENTION

1. Field of the Invention

This invention relates generally to the field of devices for data entry and manipulation in computers, and relates more particularly to an apparatus and method for entering data into a computer and manipulating virtual objects defined by the computer based on the gestures and positions of the hand, or other parts of the body, of an operator.

2. Description of the Prior Art

Input devices for computers include such devices as keyboards, digitizers, joysticks, mice, trackballs, and light pens. One function of these input devices is to position, in two dimensions, a cursor on the display screen of a computer. Once the cursor is positioned at a desired location, the computer typically will be instructed to perform an operation. The processes of positioning the cursor and selecting the operation are discrete operations, since separate motions are required to perform each operation. With a mouse, for example, cursor positioning is accomplished by moving the mouse along a surface, while selection of the operation is accomplished by pushing keys located either on the mouse or on a separate keyboard. Mastering the operation of such input devices is often difficult because the hand movements required to operate the devices do not correspond to the visual feedback presented by the display screen of the computer. Furthermore, the operator's hand(s) must be removed from the keyboard, positioned on the mouse, then returned to the keyboard.

Glove input devices also have been used to supply data to computers. U.S. Pat. No. 4,414,537, filed Sept. 15, 1981, by G. Grimes and entitled "Digital Data Entry Glove Interface," describes one such glove input device. The Grimes patent discloses a glove with sensors for detecting the flexing of finger joints, sensors for detecting contact between various portions of the hand, and sensors for detecting the orientation of the hand. The Grimes device is used to identify static hand positions representing the characters of the alphabet. Furthermore, the glove is designed to differentiate from one another a fixed number of static shapes representing the letters of the alphabet.

SUMMARY OF THE INVENTION

The present invention provides an apparatus and method for manipulating virtual objects defined by a computer according to the gestures, position, and movement of the hand of an operator. Such manipulation includes positioning a cursor or other representation of the hand of the operator with respect to virtual objects defined by the computer. Operations on those virtual objects may then be carried out according to certain gesture specifying movements of the operator's hand. The virtual objects themselves may be representations of computer input devices such as a joystick, mouse, pen, keyboard, paintbrush or other devices. More generally, the objects may be tools which themselves act on other virtual objects. For example, a virtual steering wheel may be used to drive a simulation of an automobile, or to provide input to a remote system.

The invention includes gesture sensing means coupled to the hand for detecting gesture specifying movements of the hand, such as flexing of the fingers, as well as hand position sensing means for detecting the position of the hand with respect to the display. Signal processing means are provided to receive data from the gesture sensing means and the hand position sensing means to instruct the computer to manipulate the cursor and/or virtual objects according to the movements of the operator's hand.

In one embodiment of the present invention, the gesture sensing means includes a glove assembly with attached sensors that are responsive to the degree of flex of the fingers of the operator's hand. These flex sensors are mounted on a flexible printed circuit board and are sandwiched between an inner and an outer glove. A decoding circuit for addressing the sensors is also mounted on the flexible printed circuit board, and is electrically coupled to the sensors through the flexible printed circuit board and to the computer via a detachable cable. The hand position sensing means preferably includes one or more ultrasonic transmitters affixed to the glove assembly, a stationary receiver comprising three separate spaced-apart ultrasonic receiving units, and a control circuit that measures the time delay of pulsed ultrasonic signals from the transmitter to the three receivers. The time delay provides a measure of the spatial position of the operator's hand. The signal processing means includes interface circuitry for coupling the glove to the host computer, for positioning a hand-shaped cursor on the display screen of the computer according to the position of the operator's hand, for responding to output signals from the flex sensors, and for manipulating virtual objects defined by the computer according to commands represented by the gestures and movement of the operator's hand. A database within the host computer can be employed to provide constraints, such as inertia, linkage to other objects, etc., for the objects being manipulated.

The present invention also comprises a computer data entry and manipulation apparatus and method capable of determining the dynamic gestures of an operator's hand and the spatial position of the hand. As an input device, the present invention is especially well adapted for use with a pictorial or symbolic programming language having a dynamic cursor which corresponds in shape to the shape of the glove and moves on the screen in response to movement of the glove in space. The present invention provides a basis for use of a symbolic programming language in which the physical gestures of the operator's hand are used to implement conceptually similar and easily recognizable functions or operations on virtual objects displayed on the display screen of the computer.

DETAILED DESCRIPTION OF THE PREFERRED EMBODIMENTS

FIGS. 1 through 6 of the drawings depict various preferred embodiments of the present invention for purposes of illustration only. One skilled in the art will recognize from the following discussion that alternative embodiments of the structures and methods illustrated herein may be employed without departing from the invention.

Figure 1:
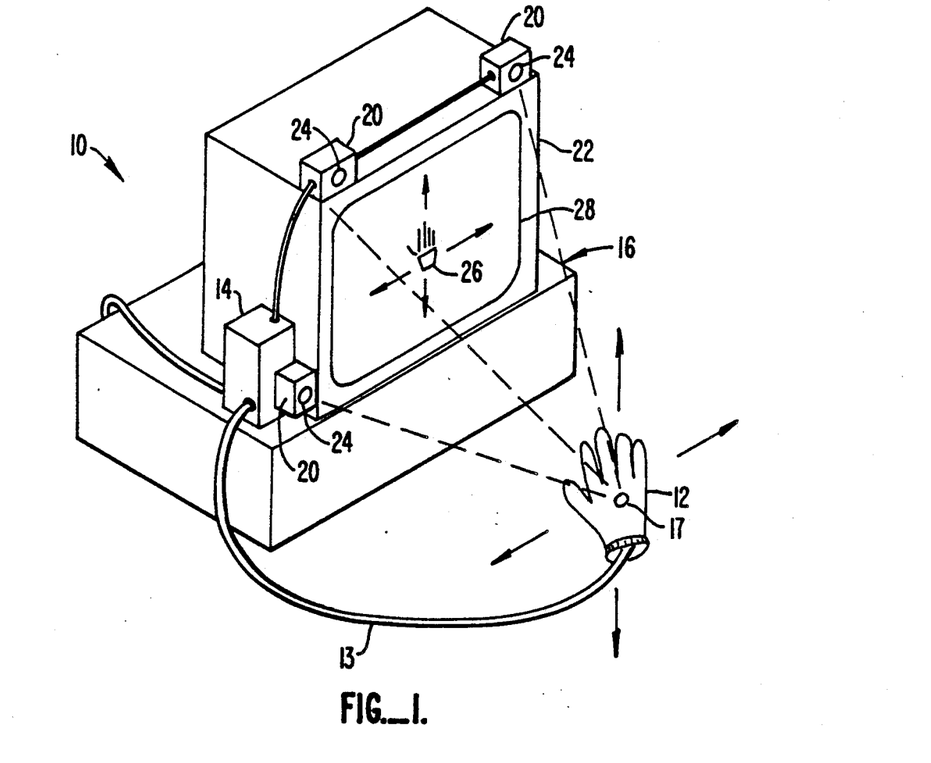
FIG. 1 is a perspective view of a preferred embodiment of the computer data entry and manipulation apparatus of the invention.

In FIG. 1, a preferred embodiment of the present invention is illustrated in its intended mode of use, namely as a computer data entry and manipulation apparatus 10. The apparatus 10 includes a glove assembly 12 electrically coupled via cable 13 to an interface circuit 14 that is, in turn, connected to a port of a host computer 16. A position sensing receiver assembly 20 consisting of three receivers disposed around the screen 28 is also electrically coupled to the interface circuit 14. As explained below, the glove assembly 12 contains sensors that detect the flexing of the fingers and other gestures of the hand of an operator, and also contains one or more ultrasonic transducers 17 for transmitting signals to receivers 20 to enable detecting the spatial position of the glove assembly 12 with respect to the computer display. The position sensing receiver assembly 20 includes three ultrasonic receivers 24 located at corners of display 28 facing toward the operator.

In operation, the glove assembly 12 is worn on the hand of an operator, and is used to position a cursor 26, typically a representation of the glove 12, on the display screen 28 of the computer 16. A computer generated virtual object is displayed on the screen 28. The spatial position of the glove assembly 12 is determined by the time delay between transmission of an ultrasonic signal by transducer 17 and the reception of that signal by the receivers 20 of the position sensing receiver assembly 20. The position and orientation of the fingers is transmitted to the interface circuit 14 by conductive cable 13, although other well-known techniques such as radio could be employed. Software within the host computer 16 converts the time delay data into orthogonal coordinates, and directs the computer 16 to display the cursor 26 on the display screen 28 accordingly. Thus, movement by the glove assembly 12 in a plane parallel to that of the display screen 28 results in corresponding movement by the cursor 26. Movement by the glove assembly 12 toward and away from the display screen 28 can be represented by varying the size of the glove representation cursor 26.

Figure 6:
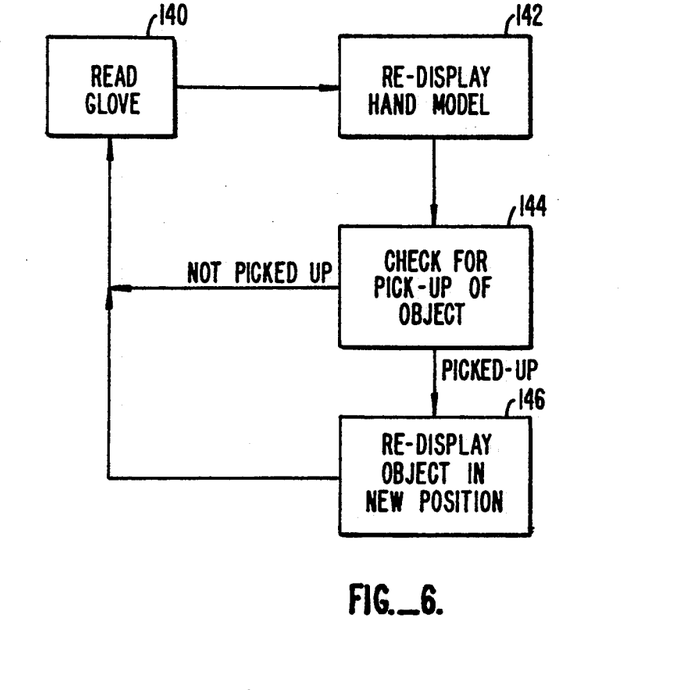
FIG. 6 is a flowchart of software employed to sense when a virtual object is picked up.

Signals from the glove assembly 12 may also enter commands into the computer 16. As described in detail below, glove assembly 12 contains sensors that respond to the gestures of the operator's hand. The software receives and interprets gesture indicating data from the sensors of the glove assembly 12 and enters commands into the computer 16 according to the gestures recognized. These commands relate to the manipulation of virtual objects created by the computer 16 and displayed on the display screen 28. For example, FIG. 6 is a flow chart illustrating software for sensing when an object has been "picked up."

Figure 2:
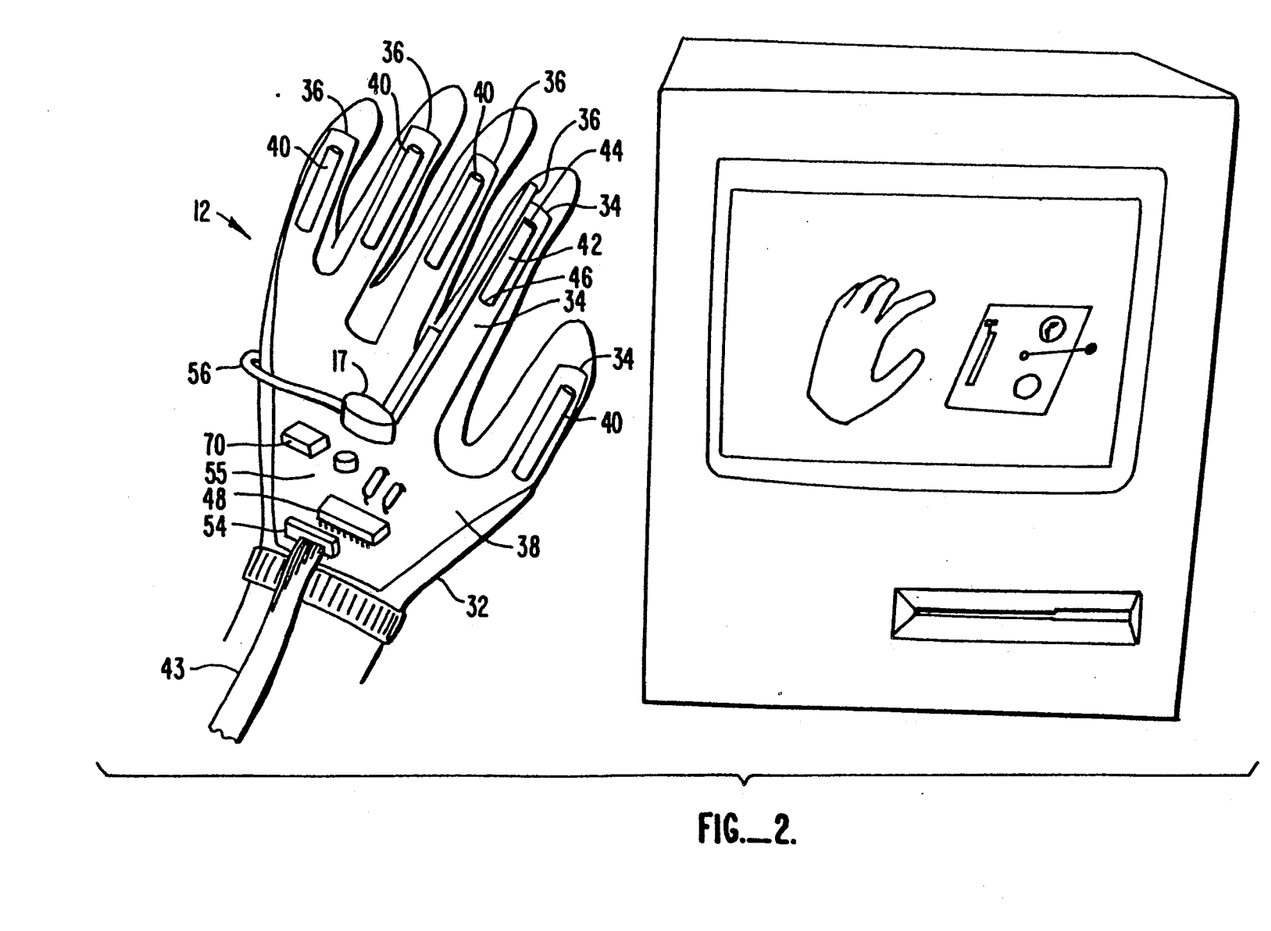
FIG. 2a is a perspective view of the glove assembly 12 shown in FIG. 1, including sensors and ultrasonic transmitter.

FIG. 2 illustrates the preferred embodiment of the glove assembly 12. An outer glove, not shown, protects the circuitry attached to the inner glove. The component parts of the glove assembly 12 are bonded or otherwise secured to an inner glove 32, which is worn on the hand of the operator during operation. In the illustrated embodiment, the sensors and electrical components of the glove assembly are soldered to and electrically interconnected by a flexible printed circuit board 34 (FIG. 2), which is itself bonded or otherwise secured to the inner glove 32. The flexible printed circuit board 34 includes five elongated portions 36 positioned along the back side of the fingers and thumb and extending from a central portion 38 positioned along the back of the hand. Preferably, the inner glove 32 is formed from a material such as stretch knitted nylon which accommodates various sizes of hands and maintains a snug fit during use. The outer glove covers and protects the components of the glove assembly 12, and improves the aesthetics of the glove assembly. Preferably, the outer glove (not shown) is composed of a light weight and durable material such as cotton.

The glove assembly 12 includes flex sensors 40, each positioned on the back side of the inner glove 32 disposed along the fingers to measure bending. The flex sensors 40 are preferably of the type that will provide a signal that is an analog representation of the degree of bend of each of the fingers and thumb. The flex sensor 40 comprises a flexible tube 42 having interior reflective walls with a light source 44 at one end and a photosensitive detector 46 at the other end. The light source 44 is preferably an infrared light emitting diode, and the photosensitive detector 46 is preferably a phototransistor. The tubing is preferably black glossy soft vinyl. The flexible tube 42 is bonded or otherwise secured to the flexible printed circuit board 34, with the electrical leads of the light source 44 and the photosensitive detector 46 soldered to appropriate conductive traces of the flexible printed circuit board. The amount of light that impinges on the photosensitive detector 46, and the corresponding amount of current flowing through the photosensitive detector, is dependent upon the amount of bend of the flexible tube 42. When the finger is extended the flexible tube 42 is generally straight and a maximum amount of light from the light source 44 impinges on the photosensitive detector 46. As the finger is flexed progressively, the portion of the tube's 42 reflective inner wall that is mutually viewed by both the light source 44 and the photosensitive detector 46 decreases, which restricts the amount of light transmitted to the photosensitive detector 46. Thus, the flex sensors 40 provide an analog signal that indicates the flexing of the operator's fingers and thumb. A detailed description of typical flex sensors may be found in U.S. Pat. No. 4,542,291, entitled "Optical Flex Sensor," which is commonly assigned.

The glove assembly 12 includes circuitry which is described below in conjunction with FIG. 3. The decoder chip 48 is soldered to appropriate conductive traces at the central portion area 38 of the flexible printed circuit board 34. The glove assembly 12 is electrically connected to the interface circuit 14 via a cable 13, which is preferably a flat ribbon cable that is releasably attached to the flexible printed circuit board 34 by a connector 54. The cable 13 also supplies power and ground signals to the components of the glove assembly 12. An optical, radio or other electromagnetic transmitter could also be employed.

As mentioned above, the glove assembly 12 includes at least one ultrasonic transducer 17, for example, a high frequency tweeter, that transmits ultrasonic signals for use in determining the spatial position of the glove assembly. Two transducers are used in some embodiments to provide roll and yaw hand orientation information, and so that at least one will be within "line-of-sight" of the receivers. The ultrasonic transducer(s) 17 is soldered to appropriate conductive traces at the central portion area 38 of the flexible printed circuit board 34, and is electrically connected to the interface electronics 14 via the cable 13. Preferably, components 55, including a transformer and transistor for controlling the ultrasonic transducer 17, are also contained in the glove assembly 12 and mounted to the flexible printed circuit board 34.

In some embodiments, to counteract possible blocking of the ultrasonic signals by the operator's hand, a flexible transmission tube 56 is utilized to conduct the ultrasonic signals to a different part of the glove assembly. Transmission tube 56 may extend in any desired direction from the ultrasonic transducer 17 to prevent shadowing. The transmission tube carries the ultrasonic signals transmitted by the ultrasonic transducer 17 and radiates those signals out an open end. The transmission tube ensures that hand gestures do not block the transmission of the ultrasonic signals to the position sensing receiver assembly 18.

In addition to the flex sensors, the glove assembly 12 may also include a hand orientation sensor 70 which provides data indicative of the orientation of the glove assembly relative to the three rotational axis of roll, pitch, and yaw. The orientation sensor 70 can be implemented in various ways, such as a three-axis accelerometer, an array of mercury potentiometers, or a bubble gauge read electro optically. In the preferred embodiment, low frequency magnetic fields like the 3SPACE ™ system are employed. This system is available from the Polhemus Navigation Sciences Division of McDonnell Douglas Electronics Co., Essex Junction, Vermont.

As an alternative to the use of spatial positioning of the glove assembly 12 for directing the two-dimensional positioning of the screen cursor 26, wrist motions may be used. For example, the forward and back flexing of the wrist can indicate vertical positioning of the screen cursor 26, while left and right flexing of the wrist can indicate horizontal positioning of the screen cursor. To achieve this additional flex sensors may be secured to the inner glove at locations surrounding the wrist joint.

Figure 3:
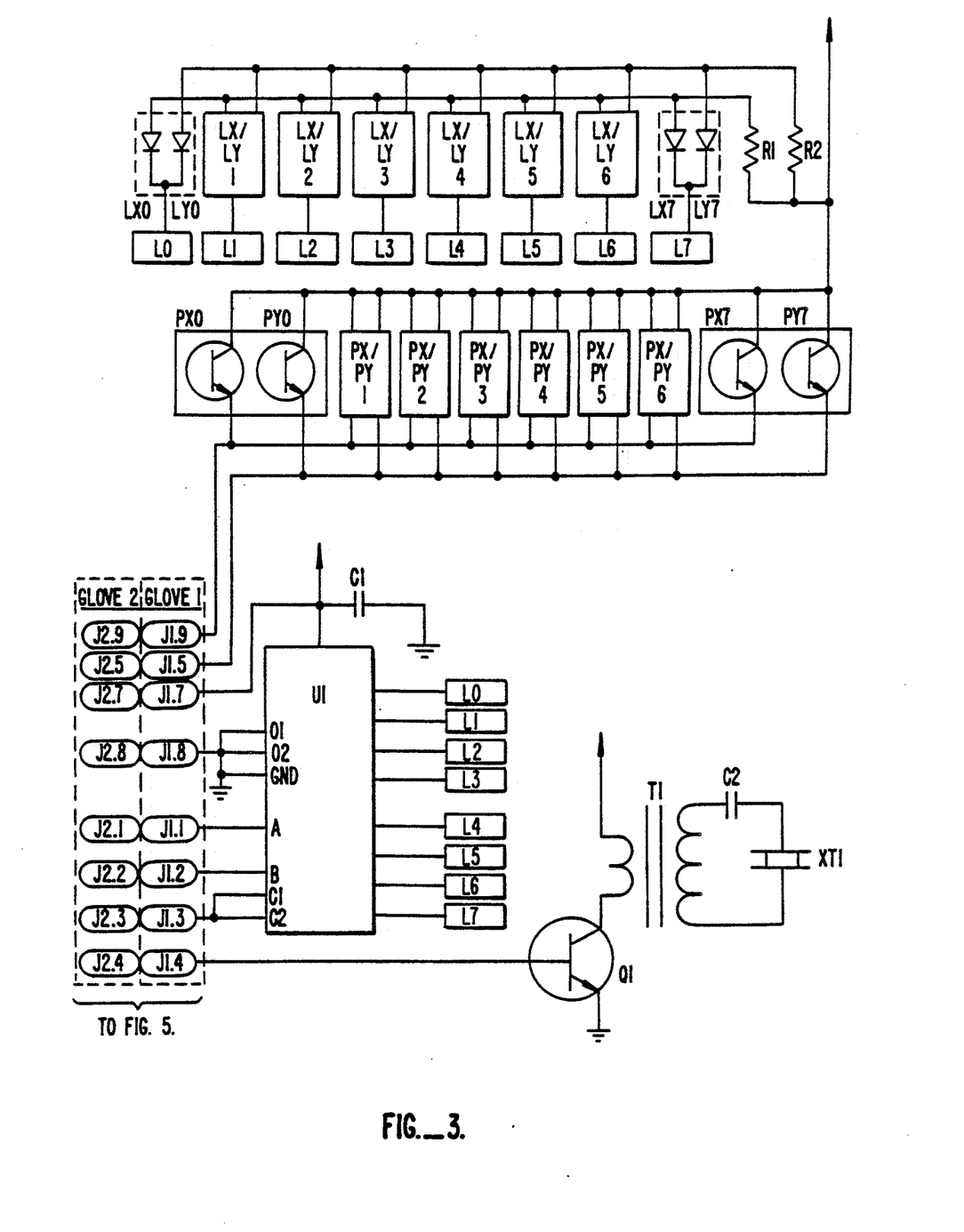
FIG. 3 is a circuit schematic of a preferred embodiment of the circuitry on glove 12.

FIG. 3 is a schematic illustrating the circuitry present on the glove according to a preferred embodiment of the invention. The circuitry shown includes a series of light-emitting diodes LX0,LY0...LX7, LY7 together with a series of solid state photodetectors PX0,PY0...PX7,PY7. As explained above, these lighte-mitting and sensing devices are employed in the bend sensors disposed on the glove, and provide direct readings of finger bending. The circuitry shown also includes a dual 2-line to 4-line demultiplexer U1, typically a 74LS156 integrated circuit. This circuit receives signals from the host computer and sequentially turns on the appropriate light source by connecting one of terminals L0–L7 to ground. The output signal from the photodetector is supplied on one of lines J1.5,J1.9 to the detector circuitry, which is described below.

The ultrasonic transmitter XT1 is controlled by a transistor Q1, preferably a type 2N2222 under control of signals supplied on line J1.4, which are supplied through a 10:1 step-up transformer T1. When the transmitter is turned on, a pulse of high frequency (about 40 kHz) sound is broadcast. The sound is received by the ultrasonic receivers 20 disposed around the monitor. Preferably, the ultrasonic transmitter XT1 is an ultrasonic piezoelectric ceramic tweeter, while the ultrasonic receiver comprises an ultrasonic piezoelectric ceramic microphone. Both such devices are commercially available from Panasonic. The time delay between the transmission of the signal by transmitter XT1 and its reception by the receivers 20 is indicative of the distance between the transmitter and each of the receivers. (Ultrasonic sound travels at about 330 meters per second.) The three distances measured between the glove and the three receivers define the position of the hand with respect to the receivers.

Figure 5:
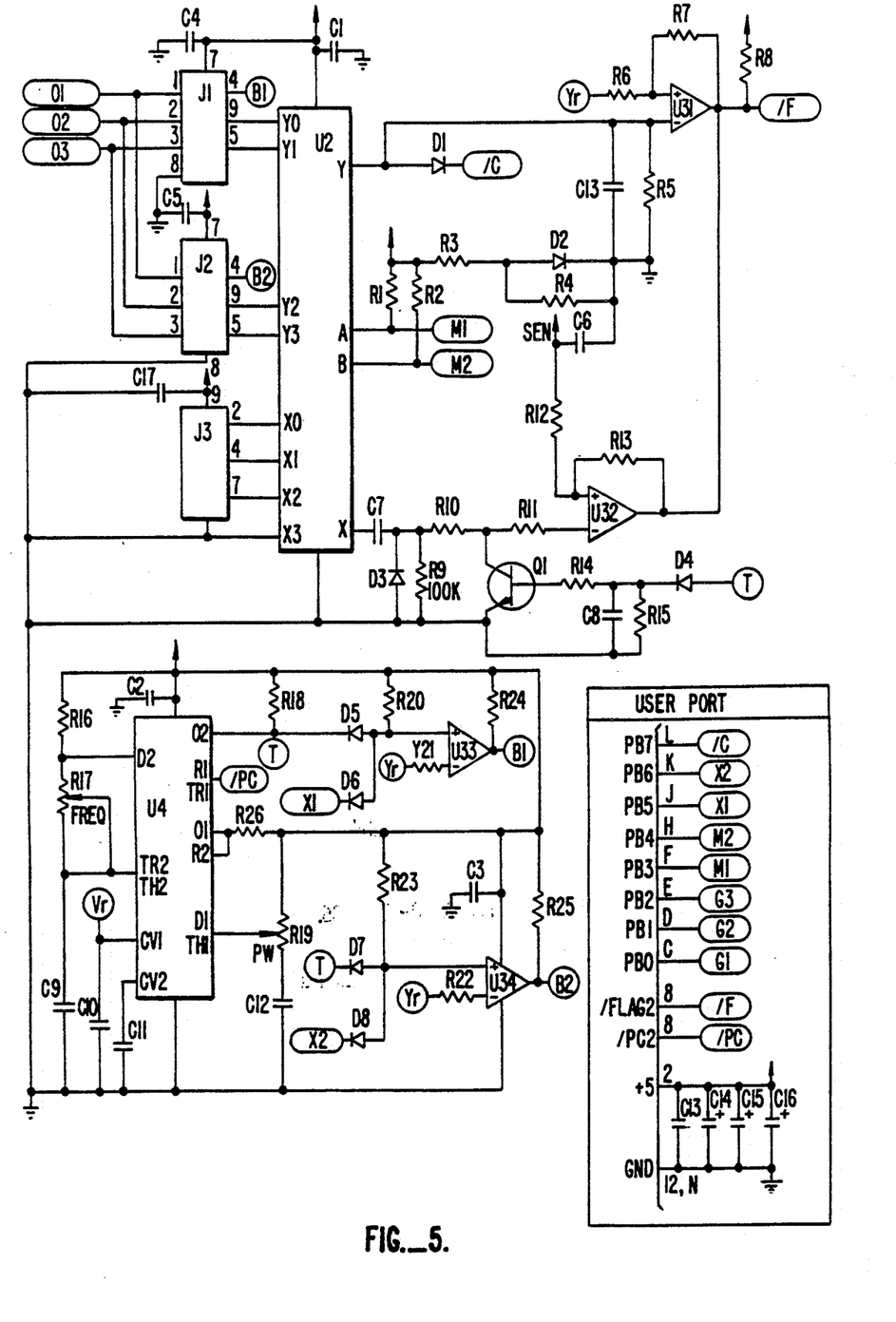
FIG. 5 is a schematic of an interface circuit used to connect a preferred embodiment of the apparatus of the invention to a host computer.

If PA is the distance from the ultrasonic transmitter to receiver A, PB the distance to receiver B and PC the distance to receiver C, and if AB and AC equal the distance between A and B, and A and C, respectively, then $$x = \frac{PA^2 - PB^2 + AB^2}{2AB} \approx K_1(PA - PB + \tfrac{1}{2}AB)$$

$$y = \frac{PC^2 - PA^2 + AC^2}{2AC} \approx K_2(PC - PA + \tfrac{1}{2}AC)$$

$$z = \sqrt{PA^2 - X^2 - Y^2} \approx K_3(PA + PB + PC)$$

where x, y and z are the distances from the origin of a rectangular coordinate system. Because the position equations require squares and square roots, the approximations are easier to calculate, requiring only addition, subtraction and scaling by constants $K_1$, $K_2$, and $K_3$ The measurement of this distance is initiated by the host computer sending a control byte to select a receiver 20 to generate a short duration high frequency pulse by triggering U4 in FIG. 5. The host then measures the time, using a counter internal to the computer, required for the reception of an ultrasonic signal. When received, this signal generates an interrupt by U32. The time between sending the control byte and the interrupt is proportional to the distance for the receiver 20 selected. By polling all three receivers sequentially at a sufficiently high frequency, the position of the glove with respect to the receivers may be readily determined.

Figure 4:
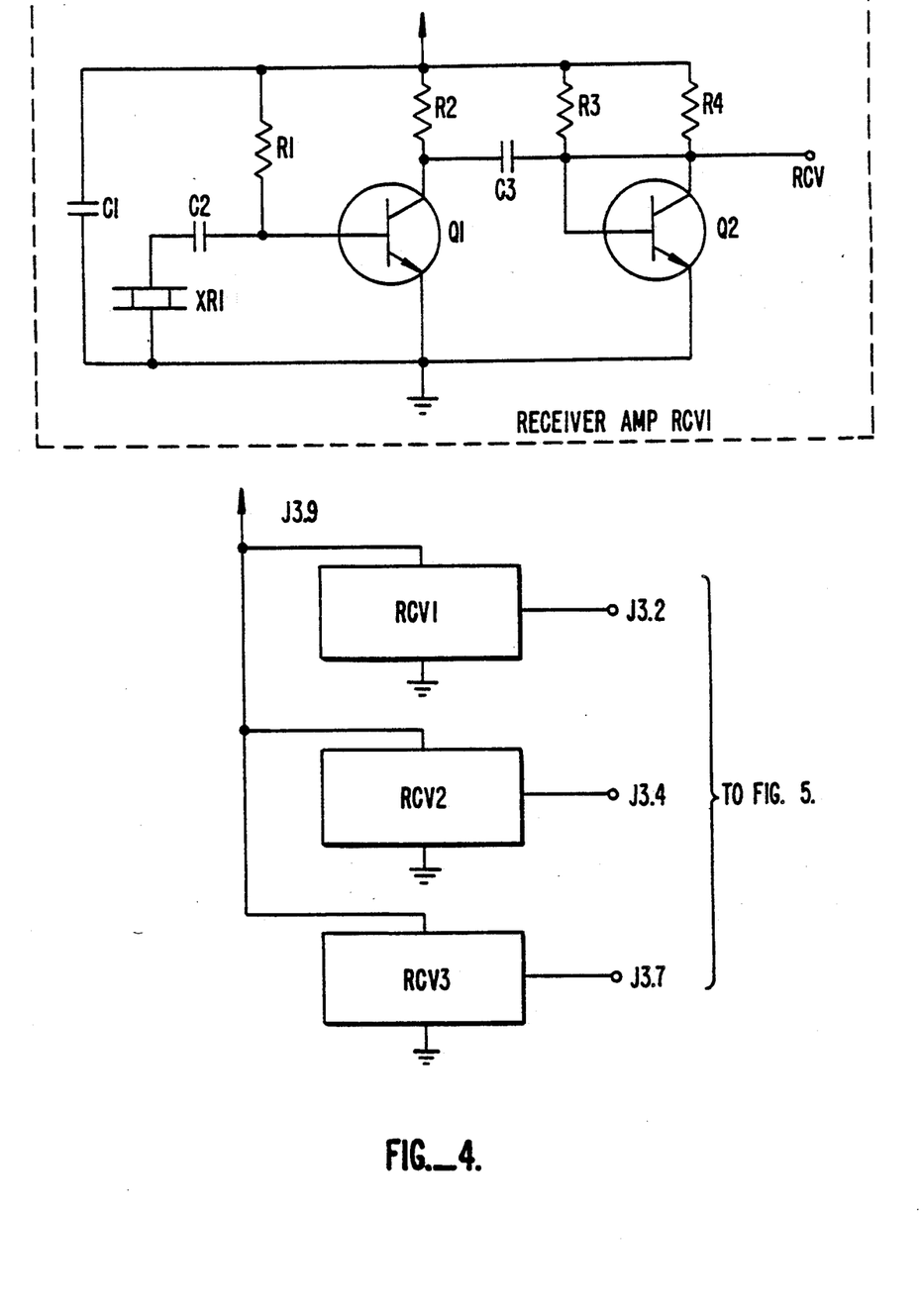
FIG. 4 is a circuit schematic of an ultrasonic receiver.

FIG. 4 is a schematic illustrating the ultrasonic receivers and the interconnections among them. As shown in the upper portion of FIG. 4, each receiver includes an ultrasonic receiver XR1 for receiving the signals, together with a two-stage amplifier comprising two transistors Q1 and Q2, preferably type 2N2222, which amplify the received signal and supply it on line RCV. The two-stage amplifiers are employed immediately next to the receiver transducer to minimize noise. Each of the receivers is disabled during and shortly after the transmission pulse by Q1 to prevent false detections. Preferably, the transmission lasts about 0.5 msec. (about 20 cycles of a 40 kHz signal), while the post transmission blanking lasts for about 0.2 msec.

FIG. 5 is a detailed schematic of the interface circuitry which couples both the glove and ultrasonic receivers to the host computer. The interface circuitry includes provision for two gloves so the operator may wear one on each hand, if necessary. In a preferred embodiment the interface circuitry adapts between a user port, for example, on a Commodore 64 computer, having the characteristics shown in FIG. 5. The circuitry shown includes three jacks, J1, J2, and J3. The output signals from glove #1 shown in FIG. 3 are connected to jack J1, while those from an optional glove #2 are connected into jack J2. The output terminals of the three receiver 20 amplifiers are connected into jack J3. The three jacks are connected to the input terminals of a dual four-channel analog multiplexer U2, preferably a type 4052 integrated circuit. This integrated circuit functions as a two pole four-throw switch and routes one of the channels from glove #1, glove #2, or the ultrasonic receivers to the detector circuitry. The channel routed to the detector circuitry is under control of terminals M1 and M2 from the user port.

The jacks J1, J2, and J3 are coupled to terminals X0...X3, Y0...Y3 of switch U2. The determination of which of these input terminals is coupled to the output terminals X and Y is made under the control of input signals M1 and M2 connected to terminals A and B of switch U2. M1 and M2 are signals supplied by the user port from the host computer. Under control of M1 and M2, one of the Y input signals will be supplied to the Y output terminal or one of the X input signals supplied to the X output terminal. The Y terminal provides bend sensor information, while the X terminal provides information from one of the ultrasonic receivers.

Assuming that the Y terminal of U2 has been selected, the host computer pulls node /C low to discharge capacitor C13. Once node /C is released, the bend sensor current supplied at output terminal Y will begin charging capacitor C13. Comparator U31 compares a reference voltage Vr with the potential on the Y output terminal. When the Y output terminal exceeds the reference voltage, which is approximately ⅔ of 5 volts, the output of comparator U31 goes to ground potential. This drop in potential on node /F is interpreted by the host computer as an interrupt signal. The delay between pulling node /C low and node /F going low is indicative of the extent of bending of the bend sensor interrogated.

The X output terminal from switch U2 provides information with respect to the time delay between transmission of the ultrasonic signal and its reception, and thereby information relating to the distance between the transmitter and the selected receiver. The ultrasonic pulse is generated by the circuitry in the lower portion of FIG. 5 explained below. In the similar manner to that described above, the output signal on terminal X of switch U2 is compared by comparator U32 to a reference voltage. Because the output signal on node X is an AC signal, diode D3 prevents it from becoming too negative. Transistor Q1 functions to turn off the detector circuit when node T is held high, while a pulse is being transmitted. Capacitor C8 and resistor R15 provide a time delay to blank operation of the detector immediately after pulse transmission to prevent interpretation of electric noise as indicative of the transmitter-receiver separation. The potentiometer R4 allows adjusting the reference potential to trim to allow for manufacturing tolerances. Once output signal X exceeds the reference voltage, the output node of comparator U32 is pulled low to create an interrupt signal on line /F, which is supplied to the host computer.

The circuitry of the remaining portion of FIG. 5 is used to generate the ultrasonic pulse for transmission by the transducer mounted on the glove. The heart of this circuit is a dual timer U4, typically a type 556 integrated circuit. Half the timer determines the transmission duration, typically about 0.5 msec., while the other half determines the transmission frequency, typically 40 kHz. Diodes D5–D8 AND the resulting pulse train with the transmit enable control bits X1 and X2 and are applied to comparators U33 and U34. These comparators drive a 1:10 step-up pulse transformer T1 through Q1 shown in FIG. 3. Potentiometer R17 is employed to set the frequency and potentiometer R19 controls the number of pulses transmitted. B1 and B2 are connected to jacks J1 and J2 and thereby provide the pulse train to the base of transistor Q1 in FIG. 10.

FIG. 6 is a flow chart which illustrates one technique by which the data entry and manipulation application of this invention may operate. Assume that an object is displayed on the screen and represented within the memory of the computer system by virtue of a table in a database indicative of the exterior appearance of the object. As the user of the system moves his hand in space, the position and orientation of the glove are continuously detected by the computer system as shown by block 140. After each determination of the position of the glove, the display 28 is updated to reflect the new glove position and orientation, as indicated by block 142. After the display is updated, the position and orientation of the glove are checked to determine whether an object has been "picked up" on the screen. This may be achieved using any desired well known algorithm, for example, by determining whether at least two points on the representation of the glove are coincident with at least two points on the object. The step is shown by block 144. If no coincidence occurs between the glove representation and object, control is returned to block 140 and the position of the glove is again read. If coincidence between the object and glove are found, control passes to block 146 and the object is displayed in its new position. Once the object has been redisplayed, control returns to block 140 so that the position of the glove may be again read.

The foregoing is a description of a preferred embodiment of the invention. It should be understood that specific details, such as component types, have been provided to explain the construction of the invention. The scope of the invention may be determined from the appended claims.

I claim:

1. Apparatus for interacting with a computer program comprising:
    display means connected to the computer for displaying objects on a screen;
    glove means adapted to be worn on a hand of a user, the glove means including gesture sensing means coupled to the glove means for detecting flexure of fingers of the user's hand, and position sensing means coupled to the glove means for detecting a position of the hand with respect to the display means;
    interface means for coupling the glove means to the computer; and
    control means for controlling a cursor indicated on the display means in response to and emulating the flexure of fingers and the position of the hand, the cursor being capable of interactivity acting upon a virtual object represented within the computer to allow communication and interaction between the user and the program.

2. Apparatus as in claim 1 wherein the position sensing means comprises transmitting means affixed to the glove for transmitting signals to receiving means disposed about the display means in close proximity thereto.

3. Apparatus as in claim 2 wherein the gesture sensing means further comprises flexure sensors affixed to the glove means to detect the extent of bending of the fingers of the user.

4. Apparatus as in claim 2 wherein the transmitting means transmits ultrasonic signals.

5. Apparatus as in claim 4 wherein the receiving means comprises a plurality of receivers of ultrasonic signals disposed about the screen.

6. Apparatus as in claim 5 wherein the plurality of receivers is three and the three receivers are not linearly arranged.

7. Apparatus as in claim 5 wherein the interface means includes circuitry coupled to the flexure sensors and to the plurality of receivers.

8. Apparatus as in claim 1 wherein the display means includes means for displaying the cursor as a representation of a hand which mirrors the position and flexure of fingers in the user's hand.

9. Apparatus as in claim 4 wherein the transmitting means comprises a plurality of transmitters.

10. Apparatus as in claim 1 wherein the interface means includes a cable connecting the glove means to the computer.

11. Apparatus as in claim 1 wherein the interface means includes an electromagnetic transmitter connecting the glove means to the computer.

12. Apparatus as in claim 1 wherein the interface means includes an optical transmitter/receiver connecting the glove means to the computer.

13. An apparatus for controlling a computer display of the type having a virtual object depicted thereon that is used for communicating and interacting with a computer program comprising:
   flex sensing means disposed in close proximity to a part of the body of the user, for sensing flexure of the associated part of the body of the user; and
   cursor display means, coupled to the flex sensing means and to the computer display, for displaying a cursor emulating the flexure of the part of the body, the cursor being capable of interactivity acting upon the virtual object to allow communication and interaction between the user and the computer program.

14. The apparatus according to claim 13 wherein the flex sensing means senses the degree of flexure of the part of the body.

15. The apparatus according to claim 14 wherein the cursor display means displays a cursor depicting the degree of flexure of the part of the body.

16. The apparatus according to claim 13 wherein the flex sensing means senses flexure of a user's hand.

17. The apparatus according to claim 16 wherein the flex sensing means senses flexure of a finger of the user's hand.

18. The apparatus according to claim 17 wherein the flex sensing means senses the degree of flexure of the user's hand.

19. The apparatus according to claim 18 wherein the cursor display means displays the degree of flexure of the user's hand.

20. The apparatus according to claim 19 wherein the flex sensing means is disposed in a glove that is worn on the user's hand.

21. The apparatus according to claim 20 wherein the cursor display means displays a representation of a hand which mirrors the flexure of fingers of the user's hand.

22. The apparatus according to claim 21 further comprising position sensing means for sensing the position of the user's hand with respect to the display.

23. The apparatus according to claim 22 wherein the cursor display means is coupled to the position sensing means and displays the position of the user's hand with respect to the display.

24. The apparatus according to claim 13 wherein the flex sensing means senses the degree of flexure of the part of the user's body and provides an analog signal to the cursor display means that indicates the degree of flexure of the part of the body;
   and wherein the cursor display means depicts the flexure of the part of the body based on the intensity of the analog signal.

25. The apparatus according to claim 24 wherein the analog signal is a function of voltage.

26. An apparatus of interacting with a virtual object represented within a computer, the virtual object being used for communicating and interacting with a computer program, comprising:
   position sensing means, disposed in close proximity to a part of a body of a user for movement therewith, for sensing the position of the associated part of the body of the user with respect to the computer;
   flex sensing means, disposed in close proximity to a part of the user's body for movement therewith, for sensing flexure of the associated part of the user's body;
   interface means for coupling the position sensing means and the flex sensing means to the computer and for controlling movement of a cursor represented within the computer in response to the position sensing means and the flex sensing means, the cursor emulating the position and flexure of the part of the user's body for interactivity acting upon the virtual object to allow communication and interaction between the user and the program; and
   wherein the computer includes contact detecting means for detecting contact between the cursor and the virtual object.

27. The apparatus according to claim 26 wherein the virtual object may be manipulated by the cursor and wherein the interface means includes object manipulating means for manipulating the virtual object with the cursor in response to the contact detecting means and in response to the position of the part of the user's body with respect to the computer.

28. The apparatus according to claim 27:
   wherein the part of the user's body is a hand.

29. The apparatus according to claim 28 wherein the flex sensing means detects flexure of a finger of the user's hand.

30. The apparatus according to claim 29 wherein the interface means represents within the computer a virtual hand which mirrors the position and flexure of the fingers of the user's hand.

31. The apparatus according to claim 30 wherein the contact detecting means detects when the virtual object is grasped by the virtual hand.

32. The apparatus according to claim 31 wherein the flex sensing means detects the degree of flexure of the fingers of the user's hand, and wherein the interface means represents within the computer the degree of flexure of the fingers of the user's hand.

33. The apparatus according to claim 32 further comprising display means for visually displaying the cursor as the position and flexure of the fingers of the user's hand.

34. The apparatus according to claim 33 wherein the display means visually displays the virtual object together with the cursor.

35. The apparatus according to claim 34, wherein the interface means causes the virtual object to be manipulated according to commands represented by the position and flexure of the fingers of the user's hand.

36. The apparatus according to claim 35 wherein the interface means causes an effect of the manipulation of the virtual object to be substantially the same as if a real object depicted by the virtual object were being manipulated in the same way of the user's hand.

37. The apparatus according to claim 36 wherein the user's hand does not act upon a real object depicted by the virtual object.

38. The apparatus according to claim 36 wherein the interface means causes the virtual object to be coupled to the virtual hand and to move together with the virtual hand when the virtual object is grasped by the virtual hand.

39. The apparatus according to claim 38 wherein the interface means further comprises linkage means for linking action of the virtual object to a second virtual object.

40. The apparatus according to claim 39 wherein the position sensing means and the flex sensing means operate without using a camera.

41. The apparatus according to claim 39 wherein the virtual object is a tool which acts upon the second virtual object.

42. The apparatus according to claim 26 wherein the flex sensing means senses the degree of flexure of the part of the user's body and provides and analog signal to the interface means that indicates the degree of flexure of the part of the body;

and wherein the interface means depicts the flexure of the part of the body based on the intensity of the analog signal.

43. The apparatus according to claim 42 wherein the analog signal is a function of voltage.

44. The apparatus according to claim 28 further comprising display means for visually displaying the cursor as the position and flexure of the part of the user's body with respect to the display.

45. The apparatus according to claim 44 wherein the display means visually displays the virtual object together with the cursor.

46. An apparatus for controlling a computer display of the type having a virtual object depicted thereon that is used for communicating and interacting with a computer program comprising:

orientation sensing means, disposed in close proximity to a part of a body of a user, for sensing the orientation of the associated part of the body of the user with respect to the display; and cursor display means, coupled to the orientation sensing means and to the computer display, for displaying a cursor emulating the orientation of the part of the user's body, the cursor being capable of interactivity acting upon the virtual object to allow communication and interaction between the user and the computer program.

47. The apparatus according to claim 46 further comprising flex sensing means, disposed in close proximity to a part of the user's body, for sensing flexure of the part of the user's body.

48. The apparatus according to claim 47 wherein the cursor display means is coupled to the flex sensing means and displays a cursor depicting the flexure of the part of the user's body.

49. The apparatus according to claim 48 wherein the flex sensing means causes the degree of flexure of the part of the user's body.

50. The apparatus according to claim 49 wherein the cursor display means displays a cursor depicting the degree of flexure of the part of the user's body.

51. The apparatus according to claim 50 wherein the part of the user's body is the user's hand.

52. The apparatus according to claim 51 wherein the flex sensing means senses flexure of a finger of the user's hand.

53. The apparatus according to claim 52 wherein the flex sensing means senses the degree of flexure of the user's hand.

54. The apparatus according to claim 53 wherein the cursor display means displays the degree of flexure of the user's hand.

55. The apparatus according to claim 54 wherein the flex sensing means and the orientation sensing means are disposed in a glove that is worn on the user's hand.

56. The apparatus according to claim 55 wherein the cursor display means displays a virtual hand which mirrors the orientation and flexure of fingers of the user's hand.

57. The apparatus according to claim 56 further comprising position sensing means for sensing the position of the user's hand with respect to the display.

58. The apparatus according to claim 57 wherein the cursor display means is coupled to the position sensing means and depicts the position of the user's hand with respect to the display.

59. The apparatus according to claim 58 wherein the cursor display means further comprises contact detecting means for detecting when the virtual object is grasped by the virtual hand.

60. The apparatus according to claim 59 wherein the cursor display means includes object manipulating means for manipulating the virtual object in response to the contact detecting means and in response to the position, flexure, and orientation of the user's hand.

61. The apparatus according to claim 46 wherein the cursor display means further comprises means for displaying a cursor depicting the roll orientation of the part of the user's body.

62. The apparatus according to claim 46 wherein the cursor display means further comprises means for displaying a cursor depicting the pitch orientation of the part of the user's body.

63. The apparatus according to claim 46 wherein the cursor display means further comprises means for displaying a cursor depicting the yaw orientation of the part of the user's body.

64. The apparatus according to claim 46 wherein the cursor display means further comprises means for displaying a cursor depicting the pitch, roll and yaw orientation of the part of the body.

65. The apparatus according to claim 47 wherein the flex sensing means sense the degree of flexure of the part of the user's body and provides an analog signal to the interface means that indicates the degree of flexure of the part of the body;

and wherein the interface means depicts the flexure of the part of the body based on the intensity of the analog signal.

66. The apparatus according to claim 65 wherein the analog signal is a function of voltage.

* * * * *

REEXAMINATION CERTIFICATE (3763rd)

United States Patent [19]

Zimmerman et al.

[11] B1 4,988,981

[45] Certificate Issued May 18, 1999

[54] COMPUTER DATA ENTRY AND MANIPULATION APPARATUS AND METHOD

[75] Inventors: Thomas G. Zimmerman, San Francisco; Jaron Z. Lanier, Palo Alto, both of Calif.

[73] Assignee: VPL Newco, Inc., Los Angeles, Calif.

Reexamination Request:
No. 90/003,122, Jul. 8, 1993

Reexamination Certificate for:
Patent No.: 4,988,981
Issued: Jan. 29, 1991
Appl. No.: 07/317,107
Filed: Feb. 28, 1989

Related U.S. Application Data

[63] Continuation of application No. 07/026,930, Mar. 17, 1987, abandoned.

[51] Int. Cl.$^6$ ........................................ G09G 5/08
[52] U.S. Cl. ........................ 345/158; 345/156; 434/45
[58] Field of Search ........................ 345/156, 157, 345/158, 161, 162, 168, 169; 434/45

[56] References Cited

U.S. PATENT DOCUMENTS

| | | |
|---|---|---|
| 3,749,810 | 7/1973 | Dow . |
| 4,210,401 | 7/1980 | Batten . |
| 4,414,537 | 11/1983 | Grimes . |
| 4,446,480 | 5/1984 | Breglia et al. . |
| 4,542,291 | 9/1985 | Zimmerman . |
| 4,565,999 | 1/1986 | King et al. . |
| 4,639,109 | 1/1987 | Hudspeth . |
| 4,682,159 | 7/1987 | Davison . |
| 4,684,231 | 8/1987 | Athy . |
| 4,754,268 | 6/1988 | Mori . |
| 4,807,202 | 2/1989 | Cherri et al. . |
| 4,861,152 | 8/1989 | Milner ................................. 345/158 |
| 4,956,794 | 9/1990 | Zeevi et al. . |

FOREIGN PATENT DOCUMENTS

| | | |
|---|---|---|
| 0 123 043 A1 | 2/1984 | European Pat. Off. . |
| 0 121 387 A2 | 3/1984 | European Pat. Off. . |
| 0 211 984 A1 | 8/1985 | European Pat. Off. . |
| 2013617 | 8/1979 | United Kingdom . |

OTHER PUBLICATIONS

"The Use of a Kinesthetic Supplement in an Interactive Graphics System", University Microfilm International (UMI), Feb. 15, 1977, Catalog No. 7702061, Issue 37, vol. 88, Paul J. Kilpatrick.

"Artificial Reality", Myron W. Krueger.

Paul Jerome Kilpatrick, The Use of a Kinesthetic Supplement in an Interactive Graphics System (1976) (Ph.D dissertation, University of N.C.–Chapel Hill), (publicly available UMI Catalog Catalog No. 7702061, Feb. 15, 1977.

Joseph J. Capowski, Remote Manipulators as a Computer Input Device (1971) (unpublished M.Sci. thesis, University of N.C.–Chapel Hill).

Wm. D. Atkinson et al., "Computing with Feelings", *Computer and Graphics*, vol. 2, pp. 97–103 (1977).

(List continued on next page.)

*Primary Examiner*—Xiao M. Wu

[57] ABSTRACT

Apparatus is disclosed for generating control signals for the manipulation of virtual objects in a computer system according to the gestures and positions of an operator's hand or other body part. The apparatus includes a glove worn on the hand which includes sensors for detecting the gestures of the hand, as well as hand position sensing means coupled to the glove and to the computer system for detecting the position of the hand with respect to the system. The computer system includes circuitry connected to receive the gesture signals and the hand position signals for generating control signals in response thereto. Typically, the control signals are used to manipulate a graphical representation of the operator's hand which is displayed on a monitor coupled to the computer system, and the graphical representations of the operator's hand manipulates virtual objects or tools also displayed by the computer.

OTHER PUBLICATIONS

Frederick P. Brooks, Jr., "The Computer 'Scientist' as Toolsmith—Studies in Interactive Computer Graphics", *Infor*mation *Processing 77*, 625–634, North–Holland Publishing Company (1977).

Frederick P. Brooks, Jr. et al., "Project GROPE—Haptic Displays for Scientific Visualization", *Computer Graphics*, vol. 24, No. 4, 177–185, Aug. 1990.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-25 and 46-66 is confirmed.

Claim 26 is determined to be patentable as amended.

Claims 27-45, dependent on an amended claim, are determined to be patentable.

26. An apparatus [of] *for* interacting with a virtual object represented within a computer, the virtual object being used for communicating and interacting with a computer program, comprising:

position sensing means, disposed in close proximity to a part of a body of a user and for movement therewith, for sensing the position of the associated part of the body of the user with respect to the computer;

flex sensing means, disposed in close proximity to a part of the user's body for movement therewith, for sensing flexure of the associated part of the user's body;

interface means for coupling the position sensing means and the flex sensing means to the computer and for controlling movement of a cursor represented within the computer in response to the position sensing means and the flex sensing means, the cursor emulating the position and flexure of the part of the user's body for interactivity acting upon the virtual object to allow communication and interaction between the user and the program; and wherein the computer includes contact detecting means for detecting contact between the cursor and the virtual object.

* * * * *